United States Patent [19]
Ekins et al.

[11] Patent Number: 5,516,635
[45] Date of Patent: May 14, 1996

[54] BINDING ASSAY EMPLOYING LABELLED REAGENT

[76] Inventors: Roger P. Ekins; Frederick W. Chu, both of Department of Molecular Endocrinology University College and Middlesex School of Medicine Mortimer Street, London W1N 8AA, United Kingdom

[21] Appl. No.: 211,800

[22] PCT Filed: Oct. 15, 1992

[86] PCT No.: PCT/GB92/01892

§ 371 Date: Jun. 22, 1994

§ 102(e) Date: Jun. 22, 1994

[87] PCT Pub. No.: WO93/08472

PCT Pub. Date: Apr. 29, 1993

[30] Foreign Application Priority Data

Oct. 15, 1991 [GB] United Kingdom .................. 9121873
Oct. 7, 1992 [GB] United Kingdom .................. 9221094

[51] Int. Cl.$^6$ .............................. C12Q 1/70; C12Q 1/68; G01N 33/53; C07H 21/04
[52] U.S. Cl. .................. 435/6; 435/5; 435/7.1; 536/24.3
[58] Field of Search .................. 435/6, 5, 91.2, 435/7.1; 536/24.3, 24.31–.33; 436/501

[56] References Cited

U.S. PATENT DOCUMENTS

| | | | |
|---|---|---|---|
| 4,372,745 | 2/1983 | Mandle et al. | 436/537 |
| 4,732,847 | 3/1988 | Stuart et al. | 435/6 |
| 4,978,625 | 12/1990 | Wagner et al. | 436/518 |
| 5,028,545 | 7/1991 | Soini et al. | 436/501 |
| 5,132,242 | 7/1992 | Cheung et al. | 436/501 |
| 5,171,695 | 12/1992 | Ekins et al. | 436/501 |

FOREIGN PATENT DOCUMENTS

| | | |
|---|---|---|
| 0267317 | 5/1988 | European Pat. Off. |
| 0301584 | 2/1989 | European Pat. Off. |
| 0360088 | 3/1990 | European Pat. Off. |
| 0396801 | 11/1990 | European Pat. Off. |
| 0333561 | 5/1993 | European Pat. Off. |
| WO8401031 | 3/1984 | WIPO |
| WO8801058 | 2/1988 | WIPO |
| WO8901157 | 2/1989 | WIPO |

OTHER PUBLICATIONS

Paper entitled "What's New on the Horizon", pp. 1–5, New York conference on Apr. 26–27, 1982 by William J. Dreyer.

*Primary Examiner*—W. Gary Jones
*Assistant Examiner*—Dianne Rees
*Attorney, Agent, or Firm*—Dann, Dorfman, Herrell and Skillman

[57] ABSTRACT

A binding assay process for an analyte, using a capture binding agent with binding sites specific for the analyte and a developing binding material capable of binding with the bound analyte or with the binding sites on the capture binding agent either occupied by the bound analyte or the remaining unoccupied binding sites, employs the capture binding agent in an amount such that only an insignificant fraction of the sample analyte becomes bound to the capture binding agent, which is preferably provided at high surface density on microspots. A label is used in relation to the developing binding material and is provided by microspheres which are less than 5 μm and carry a marker preferably fluorescent dye molecules. To determine the concentration of sample analyte, the signal strength, which represents the fractional occupancy of the binding sites on the capture binding agent by the analyte, is compared with a dose-response curve computed from standard samples. To detect an analyte comprising a single-stranded DNA sequence the analyte presence is detected by the existence of a signal. A kit for the process comprises the capture binding agent immobilised on a solid support, a developing reagent with the developing binding material attached to the microspheres and, for quantitative assays, standards of known amounts of concentrations of the analyte of interest.

16 Claims, 4 Drawing Sheets

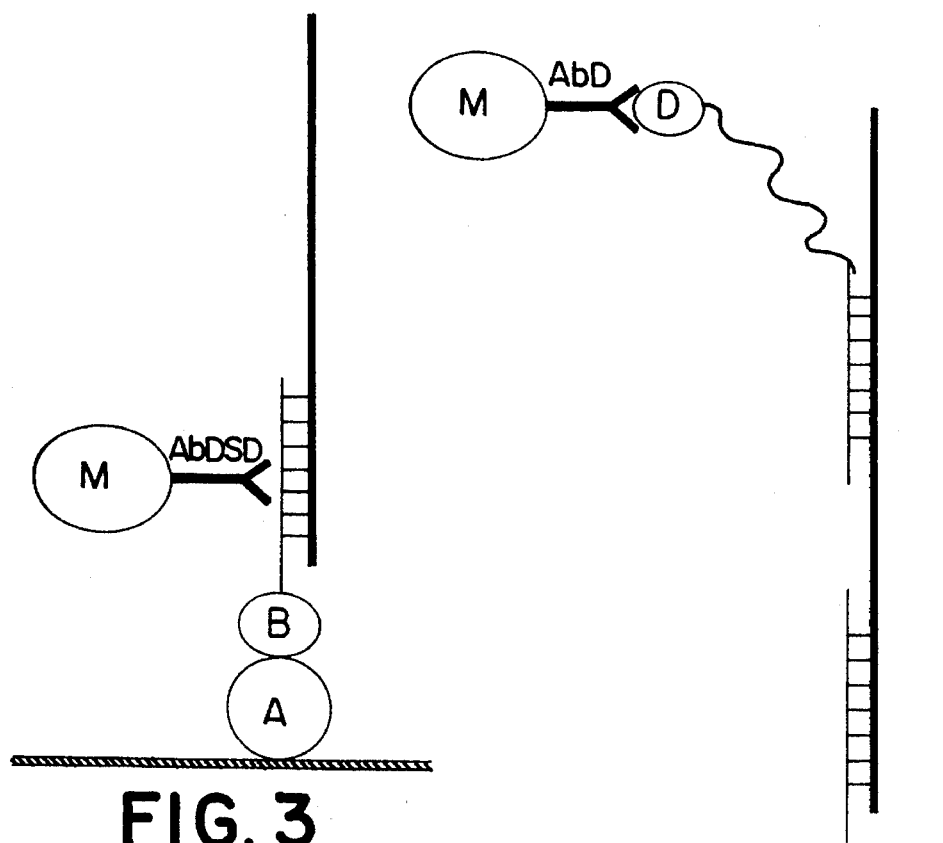
FIG. 3
FIG. 4
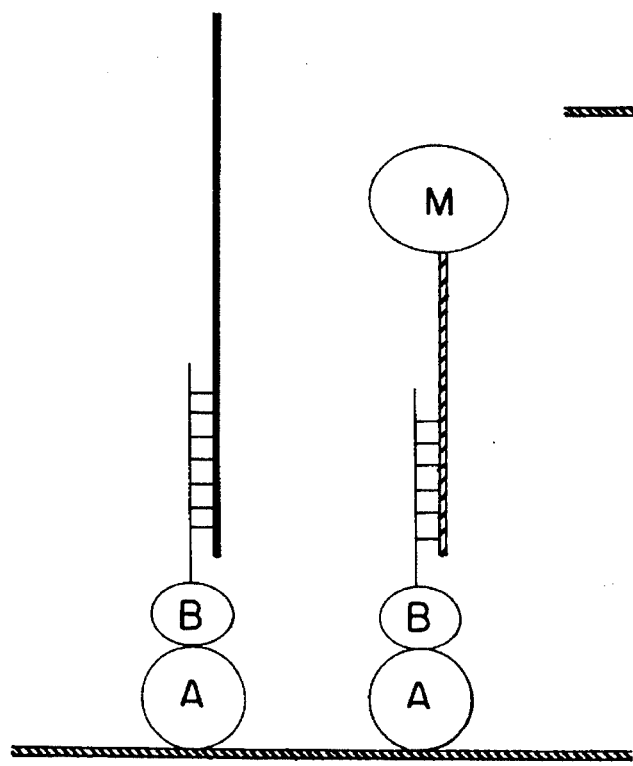
FIG. 5

BINDING ASSAY EMPLOYING LABELLED REAGENT

FIELD OF THE INVENTION

The present invention relates to binding assays employing a labelled reagent. Binding assays include immunoassays for the determination of concentrations of antigens in liquid samples, and it is also possible to use the present invention for the determination or detection of other analytes in liquid samples, including DNA sequences.

The present invention has particular relevance to non-competitive sandwich assays, that is to say assays in which a liquid sample containing an antigen or other analyte to be assayed such as a hormone is contacted with a first binding agent (such as an antibody) having binding sites on its molecule specific for the analyte whereby a fraction of the binding sites on the first binding agent representative of the concentration of the analyte in the liquid sample are occupied by the analyte. The fractional occupancy of the binding sites is then determined by a back-titration technique involving the use of a second binding material which is capable of binding with the bound analyte or with the binding sites occupied by bound analyte but not with unoccupied binding sites. Conveniently, the first binding agent will be referred to hereinafter as the capture binding agent and the second binding material will be referred to hereinafter as the developing binding material.

Non-competitive assays are to be distinguished from competitive assays in which the back-titration technique involves the use of a developing binding material which competes with the analyte for the binding sites on the capture binding agent, for example a labelled version of the analyte or another material able to bind with the unoccupied binding sites on the capture binding agent, although the present invention can also be used in such assays. In each case the extent of binding of the developing binding material is determined by the labelling of the developing binding material (or both that material and the capture binding agent), for example with a fluorescent label, and comparing the strength of the signal emitted by the bound labelled product of analyte bound to capture binding agent and developing binding material in the case of the unknown sample with the signal strengths achieved with corresponding samples of known analyte concentration which together provide a dose-response curve. One type of non-competitive sandwich assay involves the use of a labelled developing binding material and an immobilised capture binding agent which may or may not be labelled.

BACKGROUND ART

It is now well-recognised that non-competitive sandwich immunoassays generally display higher sensitivity than the more conventional competitive immunoassays. The widely accepted explanation for this higher sensitivity is the use of relatively large amounts both of the immobilised capture binding agent (usually an antibody located on a solid support) and of the labelled developing binding material (also often an antibody). By using large amounts of the antibodies, especially the capture antibody, the rate of reaction between analyte and capture antibody is increased, implying in accordance with the law of mass action that a greater amount of analyte is captured on the solid phase capture antibody in any specified time interval. Thus, the use of large amounts of capture antibody is generally perceived as crucial to the development of non-competitive immunoassays combining very high sensitivity with relatively short incubation times. (See for example Hay et al. "American Thyroid Association Assessment of Current Free Thyroid Hormone and Thyrotropin Measurements and Guidelines for Future Clinical Assays" in Clinical Chemistry, Vol 37, No. 11, (1991) at pages 2002–2008.) This approach nevertheless carries disadvantages. For example, it implies heavy consumption of antibodies which may be scarce and costly to produce. It also involves the use of various stratagems to maximise the total surface area of the solid support on which the capture antibody is deposited. For example, porous glass microspheres have been used as a solid support in sandwich assay systems, the pores greatly increasing the surface area available for antibody attachment.

Roger Ekins has previously argued, for example in WO-84/01031, WO-88/01058 and WO-89/01157, that this general perception is mistaken and that, in certain circumstances, assays which have an even greater sensitivity than that attainable under the conditions mentioned above can be developed when the unknown sample and standard samples containing the analyte are each contacted with such a small amount of the capture binding agent that only an insignificant fraction of the analyte becomes bound to the capture binding agent. (This insignificant fraction is usually less than 5% and ideally 1–2% or less of the total amount of the analyte in the sample, bearing in mind that errors in analyte determination unavoidably introduced into the measuring procedure elsewhere by limitations in the accuracy of sample and reagent manipulation, signal measurements, standardisation, temperature variation and the like are generally of the order of 10% of the analyte in the sample, although sometimes the binding of higher fractions of the analyte up to 10% or so may be tolerated when exact determination is less important.) Only when an insignificant fraction of the total amount of analyte becomes bound is the fractional occupancy F of the binding sites on the capture binding agent related to the concentration [A] of analyte in the sample (at thermodynamic equilibrium) by the equation $$F = \frac{K[A]}{1 + K[A]}$$

where K is the affinity constant of the capture binding agent for the analyte measured at equilibrium and is a constant at a given temperature and other given conditions. Before thermodynamic equilibrium is reached, the above equation also approximately applies (provided that only an insignificant fraction of the analyte in the sample has become bound to the capture binding agent at the time of measurement of the fractional occupancy, irrespective of whether a higher, significant amount becomes bound subsequently, for example by the time equilibrium is reached), subject only to the alteration that in such a situation the constant K in the equation is the apparent affinity constant of the capture binding agent for the analyte at the time of measurement.

It has also been proposed by Roger Ekins in WO-89/01157 etc to carry out such a technique using the capture binding agent spotted onto a solid support in the form of one or more microspots, for example with diameters of 1 mm$^2$ or less, using sample volumes of the order of 1 ml or less.

However, with such a system a problem may arise to provide a label which can give a sufficiently strong but sensitive signal. Doubts have also been expressed regarding sensitivities attainable using microspot assay formats on the ground that the use of very small amounts of solid-phase capture binding agent must intrinsically necessitate long incubation times and yield low sensitivity assays.

SUMMARY OF THE INVENTION

We have now found that in such a system very good results can be obtained by using as the labelling system micron or preferably sub-micron sized microspheres carrying a marker, preferably a fluorescent label. By combining the use of such a label for the developing binding material alone or for both the developing binding material and the capture binding agent with very small amounts of capture binding agent located at a high surface density on a solid support in the form of a microspot, non-competitive assay systems may be devised which are as rapid to perform as or even more rapid to perform than, and possess sensitivities comparable with or indeed greatly superior to, those of conventional sandwich systems relying upon comparatively large amounts of capture binding agent. This crucial finding, which contradicts currently accepted views on the design of high sensitivity assays and is totally unexpected, potentially forms the basis of development of a variety of superior miniaturized diagnostic devices possessing exceedingly high sensitivity whilst requiring only relatively short incubation and measurement times.

Of course, the microspheres can also be used for labelling purposes in a competitive assay system using similarly very small amounts of capture binding agent, but in such systems the limit on sensitivity may not in practice be the specific activity of the label, and corresponding or substantial increases in sensitivity due to the use of the microspheres would therefore not necessarily be achieved or even expected, although increases in rapidity can be expected.

According to the present invention there is provided a binding assay process in which the concentration of an analyte in a liquid sample is determined by comparison with a dose-response curve computed from standard samples, using a capture binding agent having binding sites specific for the analyte and a developing binding material capable of binding with the bound analyte or with the binding sites on the capture binding agent occupied by the bound analyte or with the binding sites remaining unoccupied on the capture binding agent, the capture binding agent being used in an amount such that only an insignificant fraction of the analyte in the sample becomes bound to the capture binding agent, and a label being used in the assay in relation to the developing binding material whereby the strength of the signal associated with the label is representative of the fractional occupancy of the binding sites on the capture binding agent by the analyte, in which process there is used as the label microspheres having a size of less than 5 μm and carrying a marker, preferably a fluorescent label.

In other embodiments (described below) the present invention provides a kit for use in a binding assay process, also a binding assay process for the detection or determination of an analyte comprising a single-stranded DNA sequence in a liquid sample.

DETAILED DISCLOSURE

Fluorescent microspheres of micron and submicron size have been known since about 1982 and are commercially available from many sources, e.g. from Seradyn Inc. or under the trade mark FluoSpheres from Molecular Probes Inc. Suitable microspheres have a diameter of generally less than 5 μm and preferably not more than 1 μm, more preferably of the order of 0.01 to 0.5 μm, and it is preferred to use spheres all essentially of the same standard size. The microspheres may be made of any suitable or convenient inert material such as a polymer latex, for example a polystyrene latex, which is desirably provided on its surface with either negatively charged groups such as sulphate, carboxyl or carboxylate-modified groups or positively charged groups such as amidine groups. The presence of such charged groups on the surface of the spheres allows a wide variety of proteins, such as IgG, avidin/streptavidin and BSA, to be adsorbed passively on or coupled covalently to the surfaces of the spheres at various surface densities as desired.

Although the microspheres may carry markers of various types, for example radioactive, chemiluminescent or enzyme labels, they preferably carry fluorescent labels. The fluorescent and radioactive labels are preferably contained within the microspheres, where they are shielded from outside influences, but they may (and the enzyme and chemilumienescent labels will in general) be present on the surface of the spheres. Each microsphere desirably contains large numbers of fluorescent dye molecules as labels, for example up to 10 million in 1 μm diameter spheres with smaller numbers in smaller spheres (e.g. 100 or 1,000 to 100,000 or 1 million) down to about 10 in very small spheres. The fluorescent dye molecules may be selected to provide fluorescence of the appropriate colour range (excitation and emission wavelength) compatible with standard filter sets, for example yellow/green, orange or red, or customised filter sets may be used. Fluorescent dyes include coumarin, fluorescein, rhodamine and Texas Red. The fluorescent dye molecules may be ones having a prolonged fluorescent period such that the strength of the signal emitted by them can be determined by the known time-resolved fluorescence technique after background interference has decayed, for example lanthanide chelates and cryptates. Dyes which fluoresce only in non-aqueous media can be used. Preferred fluorescent dyes for use in the microspheres are oil-soluble dyes in order to facilitate their incorporation into the interior of the microspheres. Yellow/green, orange and red FluoSpheres, which are excited very efficiently at the 488, 568 and 647 nm krypton/argon mixed gas laser lines, respectively, are presently preferred.

In use as the label for the developing binding material, or for the capture binding agent and the developing binding material, in the assay systems of the invention the microspheres may have the developing binding material, or avidin which can be used as a "universal marker" reagent and bind all biotinylated binding material, or the capture binding agent as the case may be, physically adsorbed onto the surface of the spheres. More conveniently, however, appropriately surface-modified microspheres are selected and the developing binding material (eg. antibody) or capture binding agent (eg. antibody) is covalently bonded to them either directly or through a linking grouping, such as is provided by carbodiimide activation. Thus, for example, to link the microspheres and binding material the binding material may be adsorbed onto hydrophobic sulphate-modified microspheres or covalently coupled to aldehyde-modified or carboxylate-modified hydrophilic microspheres, the latter via a water-soluble carbodiimide. When both the capture binding agent and the developing binding material are labelled with fluorescent microspheres, different dyes will of course be used in the two sets of microspheres, and the signal strength ratio can then be determined and employed for comparison as in WO 88/01058.

It will be apparent therefore that the microspheres containing many molecules of a fluorescent dye provide an amplification system (as do microspheres containing or carrying several molecules of a label of other types, e.g. a radioactive or chemiluminescent label) in the sense that one molecule or unit of the developing binding material gives rise to a signal which is due to a large number of fluorescent dye molecules or a significant number of other label molecules. Such an amplification system is thus able greatly to increase the sensitivity of these assay procedures in which the controlling factor in assay sensitivity is signal magnitude, for example when only a very small amount of capture binding agent is used and hence the amount of developing binding material is also very small.

The microspheres are primarily used in conjunction with an assay system in which the immobilised material, usually the capture binding agent (capture antibody), is deposited on a solid support in the form of one or more microspots having an area of 1 mm$^2$ down to 100 µm$^2$ or less, for example a diameter of 0.01–1 mm, although for very small microspots it may be necessary to use very small microspheres or fewer larger microspheres. The surface density of the capture binding agent on the microspot is desirably in the range 1,000 to 100,000 molecules/µm$^2$, preferably 10,000 to 50,000 molecules/µm$^2$ in the case of antibodies. For other binding agents the surface density may be within this range or above or below it but should preferably be as high as possible without sterically hindering binding of the analyte molecules. These microspots are used in conjunction with sample sizes of generally 1 ml or less, for example down to 50 or 100 µl or even less depending on the size of the microspot, the aim being to cover the microspot.

The microspot technique can be used to determine different analytes in the same or different liquid samples in a single operation by immobilising different capture binding agents on different microspots, for example 10 or more, e.g. up to 50 or more, on the same solid support and using different or identical developing binding materials labelled with the microspheres for the different binding assays. The labels (e.g. fluorescent dyes) associated with different binding assays and/or the techniques used to measure the signal strengths will be chosen to enable the results from the different assays to be differentiated. Techniques for this are known, for example from WO-88/01058.

To optimise the results achievable with the present invention a number of different features should be optimised, including the following:

i) the fractional occupancy of the capture binding agent by the analyte, ii) the size of the affinity constant of the capture binding agent for the analyte at the time when measurement occurs and, if the measurement is to be performed before equilibrium has been reached, the rate at which equilibrium is reached, iii) the surface density of the capture binding agent on its support, iv) the size of the microspots, v) the nature of the support, vi) the instrument used to measure the signal, vii) the treatment of the microspheres, for example to block unreacted sites, and viii) the nature of the buffer solutions used.

For feature i) it should be noted that the use of too much capture binding agent is to be avoided for optimal sensitivity. It is theoretically demonstrable than the highest signal/noise ratio (R) is obtained (assuming the measuring instrument itself generates zero noise) when the amount of capture binding agent falls below 0.01/K and approaches zero, K being the affinity constant between the capture binding agent and the analyte at the time of measurement. Let us define this signal/noise ratio as $R_o$. (Note that an amount of capture binding agent of 0.01/K binds <1% of analyte molecules present in the solution to which the capture binding agent is exposed.) If the area on which the capture binding agent is deposited is increased (the surface density of binding agent remaining constant) the amount of binding agent will concomitantly increase. The percentage of total analyte bound will also increase (albeit to a lesser proportional extent) but the signal/noise ratio will decrease. For example, if the area is increased 100-fold so that the amount of binding agent equals 1/K, the amount of analyte bound will rise to ≦50%, and the signal/noise ratio will fall to the order of $R_o/2$.

The relationship between the ratio R and capture binding agent concentration (ie area coated with binding agent) is shown in FIG. 1 of the accompanying drawings. This Figure is a graph of the signal/noise ratio (the continuous line where the y-axis is % of the value when the area coated with binding agent, and hence the binding agent concentration, approaches zero) and the amount of bound analyte (the dashed line, where the y-axis is % of total analyte present in the medium, assuming the total amount of analyte is very low, ie <0.0001/K) as functions of the total amount of capture binding agent (in units of 1/K, the x-axis) on the coated area. Clearly, as the area coated with capture binding agent (and hence its concentration) increases, the percentage of total analyte bound increases, but the signal/noise ratio falls. This effect is shown pictorially in FIG. 2 of the accompanying drawings, where d is the diameter in mm of the area coated with capture binding agent, [Ab] is the concentration of binding agent assuming a surface density of 0.1/K per mm$^2$, and s/n is the signal/noise ratio expressed as a percentage of the value observed as the surface area approaches zero. This Figure likewise endeavours to show that, as the coated area increases, the amount of analyte bound also increases but the signal/noise ratio and hence the sensitivity fall.

However, although the signal/noise ratio R is highest when the binding agent concentration is less than 0.01/K, it is clear that the ratio may still be acceptably high when the amount of capture binding agent used equals or even exceeds 1/K. The upper limit to the amount of binding agent coated on the microspot area is preferably 10/K. This implies a ten-fold lower sensitivity than is achievable using a 1000-fold lower amount of binding agent and it should be emphasized that, although the invention is capable of yielding very high sensitivity, it is also applicable where lower sensitivity than the maximum attainable is acceptable.

For factor ii) it should be noted that, although at first sight it might appear to be better to use a capture binding agent with a low equilibrium value of K, it is in fact generally found that for high-sensitivity assays it is better to use binding agents having higher values of K at equilibrium, e.g. $10^{11}$–$10^{12}$ or more liters/mole, and (if necessary or desired) to make the measurement before equilibrium has been reached so that at the moment of measurement only an insignificant fraction of the analyte has become bound and the effective value of K at the moment of measurement may be considerably less, e.g. $10^8$–$10^{11}$, even though a substantial fraction of the analyte might become bound if measurement were to be delayed until equilibrium had been reached. Higher effective values of K may be more appropriate where the analyte concentration is low (e.g. $10^6$ molecules/ml) and lower effective values of K may be more appropriate where the analyte concentration is high (e.g. $10^{14}$ molecules/ml). Desirably, the effective value of K is of the order of the reciprocal of the analyte concentration to be measured in the sample. It is preferred to use a capture binding agent such that, in the amounts used, equilibrium is reached within 12 hours or somewhat less but to make the measurement within about 2 hours or less, well before equilibrium is reached. This early pre-equilibrium measurement is particularly important where the capture binding agent has a very high affinity constant for the analyte, as is the case with DNA probes.

For factor iii) it should be noted that too low a surface density decreases the signal/noise ratio because the area occupied by the capture binding agent and scanned to determine the ratio increases. On the other hand too high a surface density can cause steric hindrance between adjacent capture binding agent molecules so that not all the molecules are available for binding the analyte. Preliminary experiments to see if steric hindrance is a problem can be carried out by making spots of varying binding agent surface density, labelling them with a label such as $125_I$ and measuring how the signal varies with binding agent surface density, the optimum being the highest signal. In the past, conventional practice has been to use coatings of the order of 10 µg of capture binding agent (antibody) per ml but for the present invention figures of 100–200 µg of capture binding agent (antibody) per ml may be more appropriate. The use of higher surface density also has the advantage that less of the surface is available for non-specific binding, which would otherwise increase the noise and reduce the signal/noise ratio.

For factor v) it should be noted that the support used will itself contribute to the noise level. If the level of background noise is a problem it may be preferable to use a black support rather than a white one, although this may decrease the signal level and some black supports have higher noise levels than others.

For factor vi) it is preferred to maximise the signal/noise ratio. Accordingly, the area from which the signal is measured is desirably small, preferably limited to the area of the microspot or a portion of it. Measuring the signal from a wider area beyond the microspot increases the noise level without increasing the signal level and thus decreases the signal/noise ratio. Hence it may be desirable to concentrate the illumination and to make measurements by means of a confocal microscope or other instrument achieving very precise illumination.

For factor vii) it is desirable that, after adsorption or covalent bonding of the developing binding material or capture binding agent to the microspheres has been carried out, the unreacted sites on the microspheres are blocked to avoid their non-specific binding to other biological molecules or the solid support for the capture binding agent. Blocking may be carried out with any non-interfering protein material. An albumin, particularly bovine serum albumin, is preferred. It has been found desirable to block not only with bovine serum albumin (BSA) or equivalent but also with a detergent such as TWEEN-20 or other non-ionic detergent. It is believed that there are some binding sites on the microspheres which are not blocked by BSA or other protein material alone. Microspheres blocked with BSA alone appear still to have binding sites which are capable of binding to the solid support, such as the plastic walls of the microtitre wells in which the assay is performed, or to other biological or non-biological molecules such as are present in other components of the system (eg the liquid sample), as well as being capable of non-specific binding to the capture binding agent. Use of a detergent as additional blocking agent decreases the number of such binding sites or eliminates them altogether. The detergent also helps to remove loosely bound binding agent or material or other proteins which might desorb into storage buffer and/or assay buffer and interfere with assays. Non-interfering reactants can be used to block activated groups on the surface of the microspheres, for example inert amines such as ethanolamine, glycine or lysine to block activated carboxyl groups, but any particular compounds should be checked for assay compatibility.

For factor viii) it should be noted that the choice of ingredients for the assay buffer and the wash buffer can influence the sensitivity of the results. With TSH, for example, TRIS gives a better buffer than phosphate. It may also be desirable to include a detergent in the buffer such as TWEEN 40 to reduce non-specific binding.

In other respects the immunoassay may be carried out in a known manner, for example as described in Roger Ekins' earlier patent applications as mentioned above, and incorporated herein by reference, or in the other literature. When carrying out immunoassays it is preferred, although not essential, for both the capture binding agent and the developing binding material to be antibodies. Monoclonal or polyclonal antibodies may be used and the procedure may be used to assay analytes such as hormones, nucleic acid, proteins, vitamins, drugs, viruses, bacteria, pesticides, rumour markers or other components of biological samples such as body fluids, the capture binding agent and developing binding material being appropriately chosen so as to bind to the analyte in question. The analyte in a binding assay can be a nucleotide sequence, eg a DNA oligonucleotide sequence in which case the capture binding agent and the developing binding material may both be other nucleotide sequences, which will differ from one another. The analyte may contain only one epitope for the capture binding agent or the epitope may be replicated on the analyte molecule. The polyclonal developing binding material (antibody) may react with a variety of epitopes on the analyte or the analyte capture binding agent complex, or a mixture of two or more monoclonal developing binding materials (antibodies) reacting with different epitopes may be used.

When used for nucleic acid (DNA) assays the DNA probe, a single-stranded nucleotide sequence, eg an oligonucleotide sequence of conventional or standard type, is attached as capture binding agent to a solid support and this recognises a corresponding single-standard DNA sequence constituting the analyte in a liquid sample and such sequences become bound so as to form a twin-stranded sequence. DNA probes consisting of oligonucleotide sequences are available commercially from a number of companies, e.g. Clontech Laboratories Inc., or they can be synthesised to order and/or modified (e.g. with biotin or digoxigenin) by commercial companies, e.g. British Biotechnology Products Ltd. The developing binding material may be either a labelled antibody which recognises the twin-stranded sequence as opposed to single-stranded sequences (see FIG. 3 of the accompanying drawings) or another DNA sequence which recognises another part of the DNA sequence constituting the analyte and is labelled (see FIG. 4 of the accompanying drawings), both these binding materials producing non-competitive assays. For competitive assays it is possible to use a labelled developing binding material recognising unoccupied sites of the capture binding agent, ie residual DNA probe not bound to analyte (see FIG. 5 of the accompanying drawings). In each case the label is provided in accordance with the invention by the microspheres carrying a marker, preferably molecules of a fluorescent dye contained within the microspheres. In each of FIGS. 3–5 A represents a microspot, B the capture binding agent and M the microspheres. In FIG. 3 AbDSD is an antibody to double stranded DNA, and in FIG. 4 AbD is anti-digoxigenin antibody and D is digoxigenin. Hybridisation techniques using these methodologies are already known, see for example:- Guesdon J-L (1992), "Immunoenzymatic Techniques Applied to the Specific Detection of Nucleic Acids", Journal of Immunological Methods 150, 33–49; Mantero G, Zonaro A, Albertini A, Bertolo P & Primi D. (1991), "DNA Enzyme Immunoassay: General Method for Detecting Products of Polymerase Chain Reaction", Clinical Chemistry 37/3, 422–429; Keller G. H., Huang D-P, Shih W-K & Manak M. M. (1990), "Detection of Hepatitis B Virus DNA in Serum by Polymerase Chain Reaction Amplification and Microtiter Sandwich Hybridization", Journal of Clinical Microbiology 28/6, 1411–1416; Nickerson D. A., Kaiser R., Lappin S, Stewart J, Hood L & Landegren U (1990), "Automated DNA Diagnostics Using an ELISA-based Oligonucleotide Ligation Assay", Proceedings of the National Academy of Sciences 87, 8923–8927; Wolf S. F., Haines L., Fisch J., Kremsky J. N., Dougherty J. P. & Jacobs K. (1987), "Rapid Hybridization Kinetics of DNA Attached to Submicron Latex Particles", Nucleic Acids Research 15/7, 2911–2926.

DNA assays according to the present invention therefore provide an alternative to the well-known polymerase chain reaction (PCR) for assaying DNA sequences. The PCR method is subject to certain disadvantages, including errors introduced by repeated cycles of amplification (doubling) on an initial very low concentration of DNA sequence. The present invention provides an alternative enhancement procedure in which an initial very low concentration of the DNA sequence to be detected or determined gives rise to an amplified signal in a single step because of the large number of fluorescent dye molecules contained within the microsphere to which a molecule of the developing binding material (antibody or other DNA sequence) is attached as by adsorption or direct or indirect chemical bonding.

According to a further embodiment of the invention there is provided a binding assay process for the detection of an analyte comprising single-stranded DNA sequence in a liquid sample, the process comprising contacting the sample in a non-competitive or competitive procedure with an immobilised capture binding agent which is a single-stranded oligonucleotide DNA probe capable of recognising analyte in the liquid sample and binding therewith, and with a labelled developing binding material which either is an antibody capable of recognising only twin-stranded DNA sequences formed from the probe and the analyte and of binding therewith or is an oligonucleotide DNA sequence capable of recognising and binding with either another part of the analyte or the residual probe, the developing binding material being labelled by means of microspheres having a size of less than 5 µm and carrying a marker, and, after the removal of unattached developing binding material, detecting the presence of the analyte by the existence or strength of a signal from the marker attached to developing binding material which has become bonded directly or indirectly to the immobilised capture binding agent.

Preferably, the marker is a fluorescent label, eg in the form of a large number (100 or more) of fluorescent dye molecules contained within microspheres having a size of 0.01 to 1 µm, eg 0.05–0.5 µm. It is preferred to use this technique in conjunction with the microspot technique already referred to, with the capture binding agent being immobilised as one or more microspots on a solid support at the surface densities and microspot sizes already mentioned and optionally different capture binding agents being immobilised on different microspots on the same support to enable a plurality of different DNA sequences to be detected or determined in a single operation using appropriately differentiated developing binding materials and signal detection or signal strength measurement techniques.

The procedures for forming a single-stranded DNA probe and immobilising it on a solid support are well known and described in the literature, for example the Guesdon and other references mentioned above, and standard techniques can be used for this and for the formation, e.g. by boiling, of the liquid sample containing the analyte (single-stranded DNA sequence which may or may not be present) to be detected. Coupling of the developing binding material to the microspheres may be carried out by a method known for immobilising to marker-free solid support, for example as described in the Wolf et al reference mentioned above, and the usual precautions to avoid contamination etc and other disturbing influences should be taken.

In a further embodiment the present invention provides a kit for use in a binding assay process in which the concentration of an analyte in a liquid sample is determined using a capture binding agent having binding sites specific for the analyte and a developing binding material capable of binding with the bound analyte or with the binding sites on the capture binding agent occupied by the bound analyte or with the binding sites remaining unoccupied on the capture binding agent, a label being used in relation to the developing binding material whereby the strength of the signal associated with the label is representative of the fractional occupancy of the binding sites on the capture binding agent by the analyte, the kit comprising (a) a solid support having the capture binding agent immobilised thereon, (b) a developing reagent comprising the developing binding material adsorbed or directly or indirectly chemically bonded to the surface of microspheres carrying a marker and (c) standards having known amounts or concentrations of the analyte to be determined.

Preferably, the developing reagent comprises a buffered solution containing the developing binding material attached to the microspheres, but it is also possible to provide the reagent in freeze-dried form. Similarly, the standards may also be provided as buffered solutions containing the analyte at known concentrations or in freeze dried form with instructions for appropriate reconstitution in solution form. The standards may be made up in hormone-free serum. There may be three or more standards, e.g. up to 12, of varying known analyte concentrations spanning the expected values in the unknown samples.

Preferably, the developing reagent contains the developing binding material adsorbed onto or covalently bonded to microspheres having a size of less than 5 µm and containing molecules of a fluorescent dye, and it is preferred that the solid support has the capture binding agent immobilised thereon in the form of one or more microspots of size less than 1 mm$^2$ and surface density at least 1000 molecules/µm$^2$. Different capture binding agents may be immobilised on different microspots on the same solid support and a plurality of different developing reagents and different sets of standards may be provided so that a variety of different assays for different analytes may be performed using the same solid support in a single operation, simultaneously or sequentially.

The invention is further described in the following Examples, which illustrate the preparation of the labelled developing binding material (Examples 1–4) and processes and kits according to the invention (Examples 5–12).

In the Examples concentration percentages are by weight.

EXAMPLE 1

Adsorption of Antibody or Avidin on Hydrophobic Sulfate-Microspheres 1) 0.5 ml of 2% solids suspension in pure water of surfactant-free sulphate-activated microspheres of polymer latex materials containing fluorescent dye molecules within the microspheres (FluoSpheres from Molecular Probes Inc—FluoSpheres is a Registered Trade Mark) having a diameter 0.08 or 0.12 µm was added dropwise to 2 mg of developing binding material (antibody or avidin) dissolved in 1 ml of 0.1M phosphate buffer at pH 7.4. The suspension was shaken overnight at 4° C.
2) The suspension was centrifuged at 20,000 rpm for 30 min at 10° C. (the time and speed of the centrifugation will vary with the size of the latex microspheres) to separate antibody-conjugated latex microspheres from unreacted antibody. The supernatant antibody or avidin solution was recovered for protein estimation.
3) The centrifuged pellet was dispersed in 1.0 ml of 0.1M phosphate buffer by sonication. After dispersion, the unoccupied hydrophobic sites on the microspheres were blocked by the addition of 1 ml of 2% (1% final) bovine serum albumin (BSA) and shaken for 2 hours at room temperature. The spheres were further blocked by the addition of 200 µl of 5% Tween-20 (~0.5% final) and shaken for 1 hour at room temperature. The detergent incubation step also served to get rid of loosely bound antibody/avidin which might desorb into storage and/or assay buffer and would subsequently interfere with assays.
4) The preparation was centrifuged as above and the microspheres resuspended in 2 ml of 0.1M phosphate buffer.
5) Step 4 was repeated twice. After the final centrifugation, the microspheres were dispersed in 2 ml of phosphate buffer containing 0.2% BSA and 0.01% sodium azide and stored at 4° C.

EXAMPLE 2

Covalent Coupling of Antibody or Avidin to Carboxylate-Modified Latex Microspheres by a one-step method
1) 0.5 ml of a 2% solids suspension in pure material of carboxylate-modified polymer latex microspheres containing fluorescent dye molecules (FluoSpheres from Molecular Probes Inc) and having a diameter of 0.09 µm was added dropwise to 0.5 ml of 0.015M, pH 5 acetate buffer containing 2 mg of antibody or avidin as developing binding material. The suspension was incubated at room temperature for 15 min.
2) 4 mg of EDAC [1-ethyl-3-( 3-dimethylaminopropyl)-carbodiimide] (Sigma Chemical Company) was added to the mixture and vortexed. The pH was adjusted to 6.5±0.2 with dilute NaOH (agglomeration of the latex microspheres may be observed at this stage, but they can be redispersed by gentle sonication) and the reaction mixture was mixed gently overnight at 4° C.
3) The reaction mixture was centrifuged at 20,000 rpm for 30 min at 10° C. The supernatant was recovered for protein estimation.
4) The centrifuged pellet was dispersed in 1.0 ml of 0.1M phosphate buffer by sonication. After dispersion, the unoccupied sites on the microspheres were blocked by the addition of 1 ml of 2% (1% final) bovine serum albumin (BSA) and shaken for 2 hours at room temperature. The spheres were further blocked by the addition of 200 µl of 5% Tween-20 (~0.5% final) and shaken for a further 1 hour at room temperature.
5) The preparation was centrifuged as above and the microspheres resuspended in 2 ml of 0.1M phosphate buffer.
6) Step 5 was repeated twice and, after the final centrifugation, the antibody- or avidin- conjugated microspheres were dispersed in 2 ml of phosphate buffer containing 0.2% BSA and 0.01% of sodium azide and kept at 4° C.

EXAMPLE 3

Covalent Coupling of an Antibody or Avidin to Carboxylate-Modified Latex Microspheres by a two-step method
1) 0.5 ml of the suspension of carboxylate-modified latex microspheres used in Example 2 was added to a 10 ml centrifuge tube and centrifuged at 20,000 rpm for 30 min at 10° C.
2) The centrifuged pellet was resuspended in 0.5 ml of 0.02 M phosphate buffer, pH 4.5, and centrifuged as above.
3) Step 2 was repeated.
4) 0.5 ml of a 2% solution of EDAC was added dropwise to the dispersed microspheres (agglomeration of the latex microspheres may be observed at this stage, but they can be redispersed by gentle sonication), and the reaction mixture was mixed gently at room temperature for 3 hours and centrifuged as above.
5) The centrifuged pellet was resuspended in 1 ml of 0.2M borate buffer, pH 8.5, and centrifuged as above.
6) Step 5 was repeated twice.
7) The centrifuged pellet was resuspended in 0.5 ml of borate buffer, added dropwise to 2 mg of antibody or avidin dissolved in 0.5 ml of the same buffer and mixed gently overnight at room temperature.
8) The suspension was centrifuged as above and the supernatant was kept for protein estimation.
9) The centrifuged pellet was resuspended in 1 ml of 0.1M ethanolamine in borate buffer, mixed gently for 30 min at room temperature and centrifuged as above.
10) The centrifuged pellet was resuspended in 1 ml of 1% BSA, mixed gently for 1 hour and centrifuged as above.
11) The centrifuged pellet was resuspended in 1 ml of 0.5% Tween-20, mixed gently for 1 hour and centrifuged as above.
12) The centrifuged pellet was resuspended in 1 ml of 0.02 M phosphate buffer, pH 7.4, and centrifuged as above.
13) The centrifuged pellet was resuspended in 1 ml of phosphate buffer containing 0.2% BSA and 0.01% of sodium azide and kept at 4° C.

EXAMPLE 4a

Coupling of a Mixture of Antibody and Avidin to Microspheres by Adsorption or Covalent Linkage The methodologies for the coupling of a mixture of antibody and avidin to microspheres by adsorption or covalent linkage were essentially the same as those described in Examples 1 to 3 above for the coupling of antibody or avidin to microspheres except that the antibody solution used for the reaction also contained a small amount of avidin.

EXAMPLE 4b

Labelling of a Monoclonal Anti-TSH Antibody with Texas Red
1) 1 mg of monoclonal anti-TSH antibody was dissolved in 1 ml of carbonate buffer pH 9.
2) 1 mg of Texas Red (Molecular Probes Inc.) was dissolved in 250 µl of N,N-Dimethylformamide (Sigma Chemical Company), yielding a concentration of 4 µg/µl.
3) 10 µl of the 4 µg/µl Texas Red was added to the antibody solution, vortexed and left on ice for two hours (dye to protein ratio (w/w)=0.04).
4) The Texas Red-conjugated antibody was separated from unreacted and hydrolysed dye on a PD10 Sephadex column (Pharmacia) by elution with 0.1M phosphate buffer, pH 7.4.

5) Sodium azide was added to the labelled antibody (0.1%) as preservative and the preparation was stored at 4° C.

EXAMPLE 4c

Labelling of Antibody or BSA with Biotin
1) 2 mg of antibody or BSA was dissolved in 1 ml of pH 8.5 bicarbonate buffer.
2) 2.2 mg of N-Hydroxysuccinimidyl 6-(Biotinamido) Hexanoate (Vector Laboratories) was dissolved in 55 µl of N,N-Dimethylformamide, yielding a concentration of 40 µg/µl.
3) 10 µl of the 40 µg/µl biotin was added to the antibody or BSA solution and shaken for 2 hours at room temperature (biotin to protein ratio (w/w)=0.2).
4) The reaction was terminated by the addition of 10 mg of glycine.
5) The biotin-conjugated IgG or BSA was separated from unreacted biotin on a PD10 Sephadex column (Pharmacia) by elution with 0.1M phosphate buffer, pH 7.4.
6) Sodium azide was added to the conjugated preparation (0.1%) which was stored at 4° C.

EXAMPLE 5

An Ultra-sensitive Sandwich Two-step Back-titration TSH Microspot Immunoassay employing Developing Antibody Conjugated to Fluorescent Microspheres
First Step
1) White polystyrene microtitre wells (Microlite 1 from Dynatech Laboratories) were spotted with 1 µl or less of a 200 µg/ml monoclonal anti-TSH capture antibody in 0.1M phosphate buffer at pH 7.4. The antibody droplets were aspirated immediately and the wells blocked with 1% (w/v) BSA and washed extensively with the same buffer. The antibody microspots were kept in buffer until use.
2) After rinsing with 0.05M/l Tris-HCl buffer at pH 7.75 (wash buffer), 200 µl of either standard in assay buffer or the sample was added to each well and shaken for from 30 min to several hours at room temperature (or overnight at 4° C. if maximal assay sensitivity is desired).
3) The wells were washed four times with wash buffer.
Second step
1) An aliquot of 200 µl of developing binding material antibody conjugated to fluorescent-dye containing microspheres of diameter 0.1 µm (containing ~0.01 mg antibody-conjugated microspheres) in assay buffer was added to each well and shaken for 0.5 to 1 hour at room temperature.
2) The wells were washed seven times with the wash buffer which contained 0.05% Tween-20 (w/v), aspirated until completely dry and scanned with an MRC-600 Laser Scanning Confocal Microscope (Bio-Rad Microscience). The signal emitted from each antibody microspot was quantified and the results were compared with the standard dose-response curve to determine TSH concentrations in unknown samples.

The standards used for production of the dose-response curve contained 0.01, 0.03, 0.1, 0.3, 1, 3, 10 and 30 µU TSH/ml in the assay buffer.

The assay buffer composition was:

| | |
|---|---|
| Tris-(hydroxymethyl)-aminomethane | 50 mM/l |
| Sodium chloride | 9.0 g/l |
| Bovine serum albumin | 5.0 g/l |
| Bovine globulin | 0.5 g/l |
| Tween 40 | 0.1 g/l |
| Sodium azide | 0.5 g/l |
| HCl | to a pH of 7.75 at 25° C. |

EXAMPLE 6

An assay for thyroid stimulating hormone (TSH) was carried out using two monoclonal antibodies directed at different epitopes on the TSH molecule as capture and developing antibodies, and TSH standard samples supplied by the National Institute for Biological Standards and Control. The capture antibody was deposited as microspots approximately 0.5 mm in diameter on Dynatech Microlite microtitre wells by passive adsorption, giving a surface density of about 40,000 IgG molecules/µm². The developing antibody was covalently coupled to carboxylate-modified polystyrene latex FluoSpheres 0.08 µm in diameter containing yellow/green fluorescent dye. The TSH samples were applied to the microtitre wells in amounts of about 200 µl.

Following overnight incubation, the results obtained were as plotted on FIG. 6 of the accompanying drawings, which is a graph of fluorescence intensity (y-axis) in arbitrary units against TSH concentration (x-axis) in mU/liter. The sensitivity of the assay (based on measurements of the standard deviation of the zero dose estimate) was 0.002 mU/liter. The same standards and assay buffer as those used in Example 5 were employed.

EXAMPLE 7

Example 6 was repeated except that the total incubation time was reduced to 1 hour (0.5 hour incubation of sample with capture antibody, followed by 0.5 hour incubation with developing antibody) and the size of the microspheres was increased to 0.12 µm diameter. The sensitivity of the assay was thereby increased ten-fold to 0.0002 mU/liter, based on measurements of the standard deviation of the zero dose estimate. The results are plotted in FIG. 7 of the accompany drawings, which is a graph on the same axes as FIG. 6.

EXAMPLE 8

A Single-step Ultra-sensitive Sandwich TSH Microspot Immunoassay Using Developing Antibody Conjugated to Fluorescent Microspheres
1) White polystyrene microtitre wells (Microlite 1 from Dynatech Laboratories) were spotted with 1 µl or less of a 200 µg/ml monoclonal anti-TSH capture antibody in 0.1M phosphate buffer at pH 7.4. The antibody droplets were aspirated immediately and the wells blocked with 1% (w/v) BSA and washed extensively with the same buffer. The antibody microspots were kept in buffer until use.
2) The wells were rinsed with the assay buffer used in Example 5, then 100 µl of standard in assay buffer/sample and 100 µl of developing antibody-conjugated microspheres were added to each well and shaken at room temperature for 30 minutes, or longer if maximal assay sensitivity was desired.
3) The wells were washed seven times with wash buffer containing 0.05% Tween-20 (w/v), aspirated until completely dry and scanned with the confocal microscope as in Example 5 above, the results being compared with the standard dose-response curve obtained using the standards mentioned in Example 5 to determine the TSH concentration in unknown samples.

EXAMPLE 9

Dual-labelled Ultra-sensitive Sandwich Single- or Two-step Back-titration TSH Microspot Immunoassay Using Developing Antibody Conjugated to Fluorescent Microspheres The protocols for the dual-labelled single or two-step assays are essentially the same as those for the single labelled assays described above except the unlabeled capture antibody is either labelled with Texas Red (Molecular Probes Inc.) and deposited directly on the white Dynatech Microlite microtitre wells; or it can be coupled together with avidin to latex microspheres (Molecular Probes Inc) containing red fluorescent dye and the conjugated microspheres are then allowed to bind to a biotin-labelled BSA microspot deposited previously on the microtitre wells.

EXAMPLE 10

A dual-label assay was carried out. The developing antibody was conjugated to yellow/green polystyrene latex microspheres of 0.12 μm diameter as described in Examples 1, 2 and 3. The capture antibody was deposited indirectly on Dynatech Microlite microtitre wells at a surface density of about 40,000 IgG molecules/$\mu m^2$ via biotin/avidin. The antibody was first conjugated together with avidin to polystyrene latex microspheres of 0.1 μm diameter containing red fluorescent dye, the conjugated spheres then being allowed to bind to biotinylated BSA microspots previously coated on the microtitre wells. The yellow/green and orange/red dyes were scanned using the 488 and 568 nm lines of the krypton/argon mixed-gas laser. This could be done either simultaneously or consecutively. The concentration of antigen (TSH) in the test sample was obtained by observing the ratio of the fluorescent signals from the two dyes and correlating it with the signals using the standard samples.

The results obtained are shown in FIG. 8 of the accompanying drawings, which is a graph of the ratio of the two fluorescent signals (y-axis) against TSH concentration (x-axis) in mU/liter. The sensitivity of the assay (based on measurements of the standard deviation of the zero dose estimate) was 0.0002 mU/liter.

EXAMPLE 11

Single-labelled or Dual-labelled Ultra-sensitive Sandwich Single- or Two-step Back-titration TSH Microspot Immunoassay Using Biotinylated Developing antibody and a Universal Reagent of Avidin conjugated Fluorescent Microspheres In contrast to the assay systems described in Examples 5 to 10, a universal marker reagent of avidin conjugated fluorescent microspheres was used in this Example to tag indirectly the bound developing antibody which had been labelled with biotin.

Although this assay system requires an additional step of the addition of avidin microspheres after the completion of the immunological reactions, the advantage of being able to use a "universal marker" outweighs this minor drawback. The "universal marker" system would be particularly useful in a microspot multianalyte system described by Roger Ekins in WO-89/01157 because of the considerable improvements in assay sensitivity that can be expected as a result of the reduction in non-specific binding from employing a single universal avidin-microsphere preparation rather than the large number (equivalent to the number of simultaneous assays being performed) of developing antibody conjugated microsphere preparations that would otherwise be required.

EXAMPLE 12

Microspot DNA Sequence Assay Methodologies

Non-competitive methodoloaies (qualitative and quantitative assays)

EXAMPLE 12a

Microspot sandwich DNA sequence assay using a biotinylated solid-phased capture DNA probe and anti-double-stranded DNA antibody conjugated to microspheres containing fluorescent dye.

1) Microlite 1 microtitre wells were spotted with 1 μl or less of 100 μg/μl Avidin DX (Vector Laboratories) by adsorption for 1 hour at room temperature, blocked for 20 min with 200 μl of 0.1M Tris-HCl pH 7.5 containing 0.15M NaCl, 0.05% Tween 20, 0.5% BSA and 100 μg/ml salmon sperm DNA and washed with Tris-HCl containing 0.05% Tween 20.
2) 5 to 100 ng of the biotinylated capture DNA probe purchased from Clontech Laboratories in 100 μl of Tris EDTA was added to the avidin DX coated wells, incubated with shaking for 2 hr at room temperature and washed with Tris-HCl containing 0.05% Tween 20.
3) In a modification of the procedure described in the Manero et al reference (see above) samples were prepared by boiling 0.5 ml aliquots of the unknown samples for 10 min, then cooled rapidly on ice, diluted with hybridization buffer containing: 1X SSC (150 mmol/l of NaCl and 15 mmol of trisodium citrate per liter), 2X Denhardt's solution (0.4 g of BSA, 0.4 g of Ficol and 0.4 g of polyvinylpyrrolidone per liter), 10 mmol/l Tris-HCl pH7.5, and 1 mmol/l EDTA. For a quantitative assay, the prepared samples or, as the case may be, standards containing single-stranded target DNA in known amounts and in the same hybridisation buffer were added to the wells (positive and negative controls rather than the standards were added to the other wells for the qualitative tests), incubated with shaking at 50° C. for 1 hour and washed with PBS containing 0.05% Tween 20.
4) 200 μl of anti-double-stranded DNA antibody conjugated to fluorescent microspheres of diameter 0.1 μm (FluoSpheres) by the method described in Example 3 and in PBS containing 0.5% BSA and 0.05% Tween 20 was added, incubated with shaking for 1 hour at room temperature, washed with PBS-Tween 20 and scanned with the confocal microscope as described in Example 5.

EXAMPLE 12b

Microspot sandwich DNA sequence assay using a biotinylated solid-phased capture DNA probe, a complementary but non-overlapping developing DNA probe labelled with digoxigenin and anti-digoxigenin antibody conjugated to microspheres containing fluorescent dye.

1) The avidin-biotinylated capture DNA probe microspots were prepared as described in Example 12a.
2) The hybridisation step was carried out as described in Example 12a.
3) 5 to 10 ng of the complementary but non-overlapping developing DNA probe labelled with digoxigenin (as described in the Nickerson et al reference above) in 100 μl of hybridization buffer was added, incubated with shaking at 50° C. for 1 hour and washed with PBS-Tween 20.

4) 200 μl of the anti-digoxigenin antibody-conjugated fluorescent microspheres of about 0.1 μm diameter (FluoSpheres) in PBS containing 0.5% BSA and 0.05% Tween 20 were added, incubated for 1 hour at room temperature with shaking, washed with PBS-Tween 20 and scanned with the confocal microscope.

EXAMPLE 12c–12e

Microspot sandwich DNA sequence assay using an unlabelled solid-phased capture DNA probe and either anti-double-stranded DNA antibody conjugated to microspheres containing fluorescent dye or a complementary but non-overlapping biotinylated developing DNA developing probe and avidin-conjugated microspheres containing fluorescent dye or a complementary but non-overlapping developing DNA probe labelled with digoxigenin and antidigoxigenin antibody conjugated to microspheres containing fluorescent dye may be carried out in a similar manner with appropriate changes.

Competitive DNA sequence assay methodology (quantitative and qualitative)

EXAMPLE 12f

Microspot DNA sequence assay using a biotinylated solid-phased capture DNA probe and a competitive material of target DNA sequence labelled with microspheres containing fluorescent dye.

1) The avidin-biotinylated capture DNA probe microspots were prepared as described in Example 12a.
2) Samples were prepared by boiling 0.5 ml aliquots of the unknown samples for 10 min, then cooled rapidly on ice, and diluted with hybridization buffer containing: 1X SSC (150 mmol/l of NaCl and 15 mmol of trisodium citrate per liter), 2X Denhardt's solution (0.4 g of BSA, 0.4 g of Ficol and 0.4 g of polyvinylpyrrolidone per liter), 10 mmol/l Tris-HCl pH 7.5, and 1 mmol/l EDTA. For a quantitative assay, the prepared sample plus the competitive material of target DNA sequences generated by polymerase chain reaction and labelled with fluorescent microspheres of diameter 0.1 μm (FluoSpheres) prepared using a technique modified from that described in the Wolf et al reference mentioned above for the attachment of DNA to latex particles, or standards containing single-stranded target DNA plus the competitive material and in the same hybridization buffer were added to the wells (positive and negative controls plus the competitive material instead of the standards plus the competitive material were added for the qualitative tests), incubated with shaking at 50° C. for 1 hour, washed with Tris-HCl containing 0.05% Tween 20 and scanned as described in Example 5.

As indicated above, these very high sensitivities for non-competitive immunoassays are unexpected in the light of the currently accepted views on assay design. Some increase in sensitivity would be expected in any assay format, once the idea of using microspheres in accordance with the invention has been appreciated, because of the increased number of molecules of label attached to each molecule of developing binding material, this resulting in an effective increase in specific activity of the labelled developer molecules. However, this effect alone might not be expected to result in assay designs departing so markedly from conventional concepts in this field and requiring in particular very small amounts of capture binding agent.

Two further possible explanations for these unexpected findings can perhaps be advanced. The first is that by confining a very small number of capture binding agent molecules at high surface density to a very small area in the form of a microspot the signal/noise ratios obtained in any finite incubation time may be improved as compared with those obtained in conventional designs in which very large amounts of capture antibody are distributed over large surface areas. The second is that when analyte molecules are located between two solid surfaces on which the capture binding agent and developing binding material molecules are respectively located (viz the microspheres and the microtitre wells in which the assay is performed) binding sites on the analyte molecules may become bound to multiple developing binding material molecules if the analyte contains the same epitope replicated on its surface or if the developing binding material is a polyclonal antibody or if more than one monoclonal antibody directed at different epitopes on the analyte is used as developing material, thus increasing the effective affinity of the developing binding material. This implies that the surface density of developing binding material molecules on the microspheres is likely to represent an important determinant of the sensitivities achieved.

We claim:

1. A binding assay process for determining the concentration of one or more analytes in a liquid sample using a capture binding agent having binding sites specific for each analyte expected to be present in the sample and a developing binding material capable of binding to bound analyte, to binding sites of the capture binding agent occupied by bound analyte or to binding sites remaining unoccupied by the analyte, the capture binding agent for a given analyte being immobilized at high density on a support in the form of one or more microspots each having an area less than 1 mm$^2$, and wherein labelled microspheres having a diameter less than 5 μm being used in the assay in relation to the developing binding material, so that the strength of the signal from the label is representative of the fractional occupancy of the binding sites of the capture binding agent, thereby allowing the concentration of the analyte to be determined.

2. The process of claim 1, wherein the capture binding agent specific for a given analyte is used in a small amount that binds less than 5% of the analyte in the sample.

3. The process of claim 2, wherein less than 0.1 V/K moles of a capture agent specific for a given analyte are used, where V is the sample volume in liters and K is the effective affinity constant of the capture binding agent for the analyte under the conditions of the assay.

4. The process of claim 1, wherein the capture binding agent is immobilized at a surface density of 10,000 to 50,000 molecules/μm$^2$.

5. The process of claim 1, wherein the microspots have an area less than 100 μm$^2$.

6. The process of claim 1, wherein the concentration of a plurality of analytes is determined in the same operation using a plurality of different capture binding agents, each capture binding agent having binding sites specific for a given analyte in the sample.

7. The process of claim 6, wherein one or more developing binding materials are used in the assay, the developing binding materials and the labelled microspheres being capable of binding to each other, so that the same label is used in relation to the developing binding materials, with the microspots containing different capture binding agent being distinguished apart by their location on the support.

8. The process of claim 7, wherein one of the microspheres and the developing binding materials is conjugated to biotin and the other to avidin or streptavidin.

9. The process of claim 1, wherein the label is contained within the microspheres.

10. The process of claim 1, wherein the label is a fluorescent label.

11. The process of claim 1, wherein the microspheres are blocked to minimize their non-specific interactions with other materials.

12. The process of claim 1, wherein the capture binding agent and the developing binding material are antibodies.

13. The process of claim 1, wherein the analyte is a nucleic acid sequence, the capture binding agent is an oligonucleotide sequence capable of binding the analyte and the developing binding material is oligonucleotide sequence or an antibody capable of hybridizing to the analyte.

14. A binding assay process for detecting the presence of one or more target nucleic acid sequences in a liquid sample using one or more capture binding agents comprising an oligonucleotide sequence capable of hybridizing to a given target nucleic acid sequence and a developing binding material comprising an oligonucleotide sequence capable of hybridizing to the bound target nucleic acid sequence, the capture binding agent for a given target nucleic acid sequence being immobilized at high density in the form of one or more microspots each having an area less than 1 mm$^2$, and wherein labelled microspheres having a diameter less than 5 μm are used in the assay in relation to the developing binding material, so that the signal from the label indicates the presence of the target nucleic acid sequence, thereby allowing the presence of said one or more target nucleic acid sequences to be detected.

15. A kit for determining the concentration of one or more analytes in a liquid sample, the kit comprising:

one or more capture binding agents, each capture binding agent having binding sites specific for a given analyte expected to be present in the sample, wherein the capture binding agents are immobilized at high density on a support in the form of one or more microspots, each microspot having an area less than 1 mm$^2$; and, one or more developing binding materials, each developing binding material being capable of binding to a given bound analyte, to binding sites of a given capture binding agent occupied by bound analyte or to binding sites of a given capture binding agent remaining unoccupied by the analyte;

wherein labelled microspheres having a diameter less than 5 μm are used in the assay in relation to the developing binding material, so that the strength of the signal from the label is representative of the fractional occupancy of the binding sites of a given capture binding agent, thereby allowing the concentration of the analyte to be determined.

16. The kit of claim 15, further comprising standards containing known amounts or concentrations of analyte.

* * * * *

(12) EX PARTE REEXAMINATION CERTIFICATE (6208th)
United States Patent
Ekins et al.

(10) Number: US 5,516,635 C1
(45) Certificate Issued: Apr. 29, 2008

(54) BINDING ASSAY EMPLOYING LABELLED REAGENT

(75) Inventors: Roger P. Ekins, London (GB); Frederick W. Chu, London (GB)

(73) Assignee: Multilyte Limited, London (GB)

Reexamination Request:
No. 90/006,853, Nov. 10, 2003

Reexamination Certificate for:
Patent No.: 5,516,635
Issued: May 14, 1996
Appl. No.: 08/211,800
Filed: Jun. 22, 1994

(22) PCT Filed: Oct. 15, 1992
(86) PCT No.: PCT/GB92/01892

§ 371 (c)(1),
(2), (4) Date: Jun. 22, 1994

(87) PCT Pub. No.: WO93/08472

PCT Pub. Date: Apr. 29, 1993

(30) Foreign Application Priority Data

Oct. 15, 1991 (GB) ............................................... 9121873
Oct. 7, 1992 (GB) ............................................... 9221094

(51) Int. Cl.
*C12Q 1/68* (2006.01)
*G01N 33/58* (2006.01)

(52) U.S. Cl. ................................ 435/6; 435/5; 435/7.1; 536/24.3

(58) Field of Classification Search ................. 435/7.1, 435/6, 91.2; 436/501
See application file for complete search history.

(56) References Cited

U.S. PATENT DOCUMENTS 1,711,742 A 5/1929 Nordlander 3,001,915 A 9/1961 Fonner
(Continued)

FOREIGN PATENT DOCUMENTS

EP 0 015 687 A 4/1983
EP 0267317 5/1988

(Continued)

OTHER PUBLICATIONS

Blaaderen et al. Langmuir, 1992, 2921–2931.
Roger Ekins, "Radioimmunoassay is Not Dead—Yet", paper presented in Future Directions for Nonisotopic Immunoassays, Tarrytown, New York, May 10–11, 1982.

(Continued)

*Primary Examiner*—Padmashri Ponnaluri

(57) ABSTRACT

A binding assay process for an analyte, using a capture binding agent with binding sites specific for the analyte and a developing binding material capable of binding with the bound analyte or with the binding sites on the capture binding agent either occupied by the bound analyte or the remaining unoccupied binding sites, employs the capture binding agent in an amount such that only an insignificant fraction of the sample analyte becomes bound to the capture binding agent, which is preferably provided at high surface density on microspots. A label is used in relation to the developing binding material and is provided by microspheres which are less than 5 μm and carry a marker preferably fluorescent dye molecules. To determine the concentration of sample analyte, the signal strength, which represents the fractional occupancy of the binding sites on the capture binding agent by the analyte, is compared with a dose-response curve computed from standard samples. To detect an analyte comprising a single-stranded DNA sequence the analyte presence is detected by the existence of a signal. A kit for the process comprises the capture binding agent immobilised on a solid support, a developing reagent with the developing binding material attached to the microspheres and, for quantitative assays, standards of known amounts of concentrations of the analyte of interest.

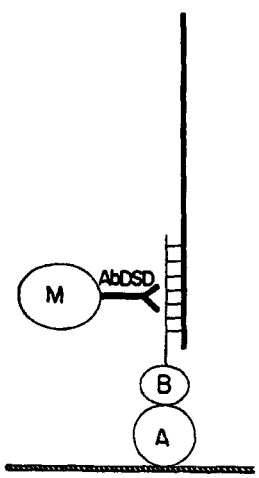

U.S. PATENT DOCUMENTS

Figure 1:
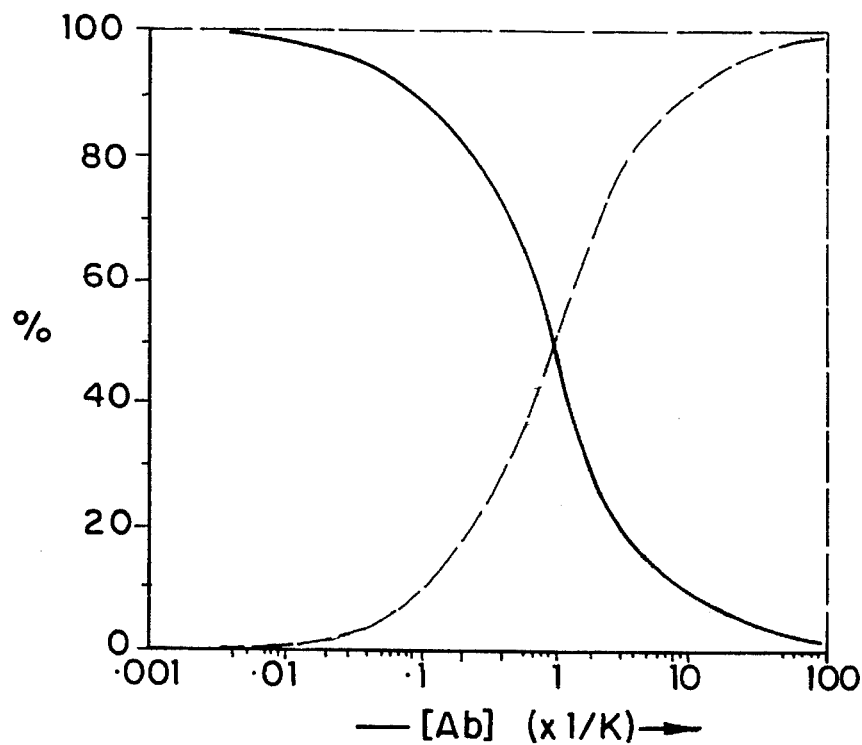
Figure 2:
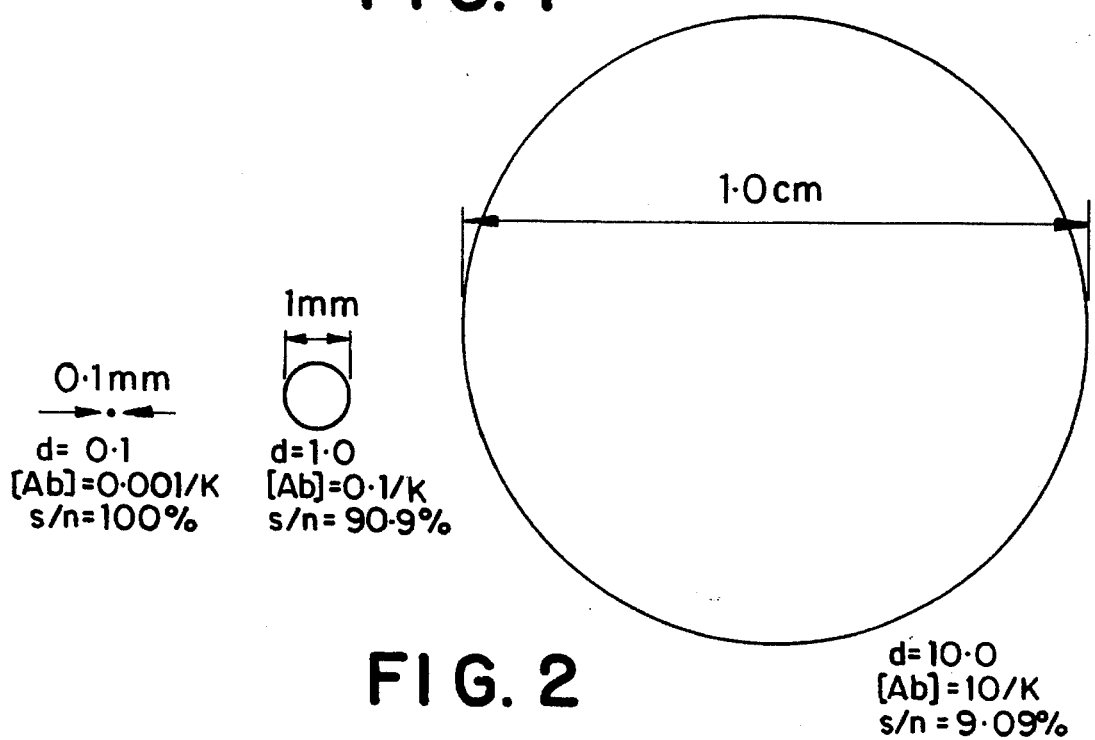
Figure 6:
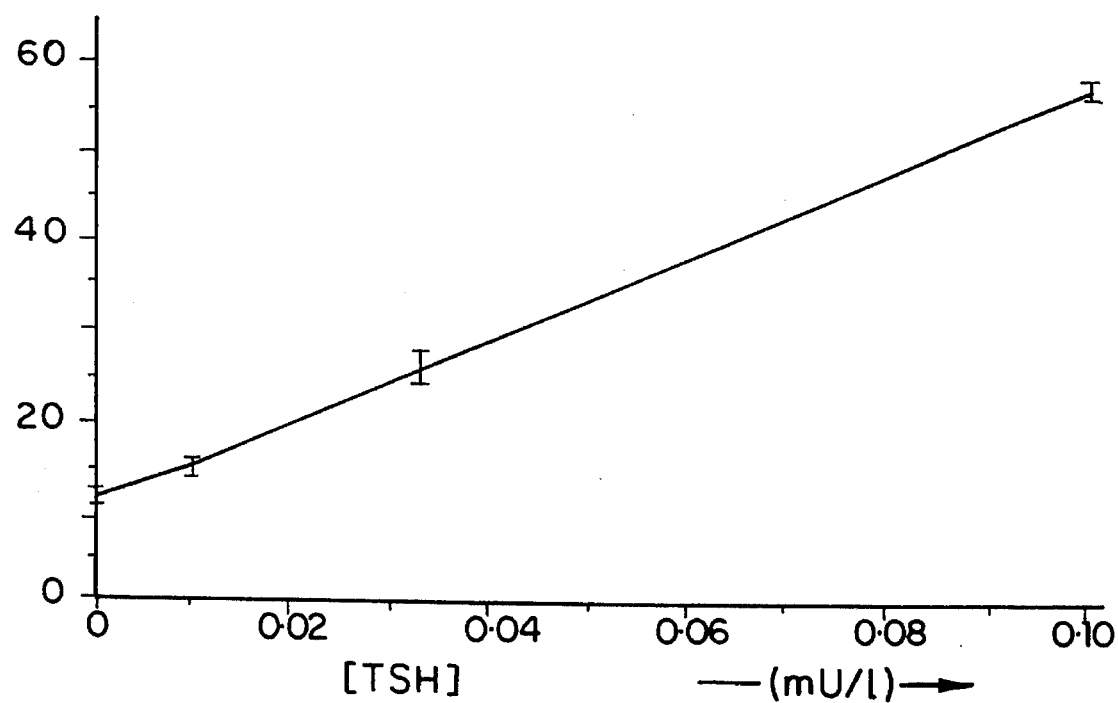
Figure 7:
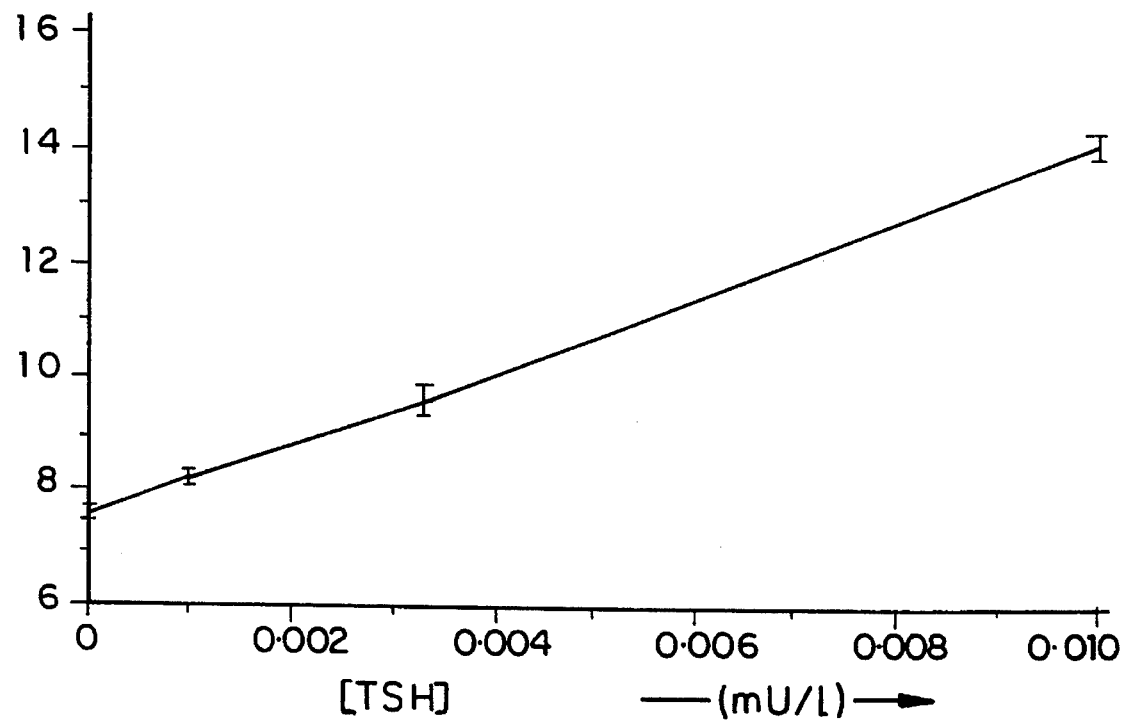
Figure 8:
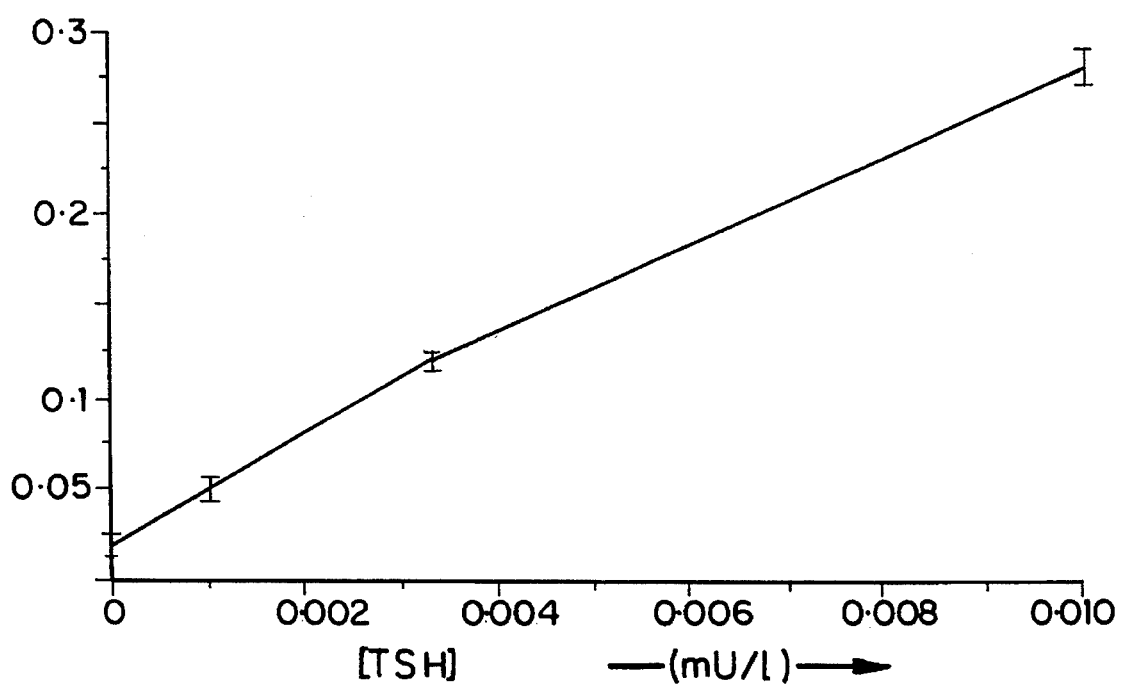

| | | | |
|---|---|---|---|
| 4,054,646 | A | 10/1977 | Giaever |
| 4,120,754 | A | 10/1978 | Barendsz et al. |
| 4,299,916 | A | 11/1981 | Litman et al. |
| 4,301,115 | A | 11/1981 | Rapkin et al. |
| 4,372,745 | A | 2/1983 | Mandle et al. |
| 4,385,126 | A * | 5/1983 | Chen et al. ........... 436/518 |
| 4,402,819 | A | 9/1983 | Rechnitz et al. |
| 4,487,839 | A | 12/1984 | Kamentsky |
| 4,647,544 | A | 3/1987 | Nicoli et al. |
| 4,732,847 | A | 3/1988 | Stuart et al. |
| 4,880,750 | A | 11/1989 | Francoeur |
| 4,978,625 | A | 12/1990 | Wagner et al. |
| 5,028,545 | A | 7/1991 | Soini et al. |
| 5,132,242 | A | 7/1992 | Cheung et al. |
| 5,156,953 | A | 10/1992 | Litman et al. |
| 5,171,695 | A | 12/1992 | Ekins et al. |
| 5,432,099 | A * | 7/1995 | Ekins ................. 436/518 |
| 5,486,452 | A | 1/1996 | Gordon et al. |

FOREIGN PATENT DOCUMENTS

| | | |
|---|---|---|
| EP | 0301584 | 2/1989 |
| EP | 0 304 202 | 2/1989 |
| EP | 0360088 | 3/1990 |
| EP | 0396801 | 11/1990 |
| EP | 0333561 | 5/1993 |
| GB | 2 099 578 A | 11/1982 |
| WO | 84/01031 | 3/1984 |
| WO | 84/03151 | 8/1984 |
| WO | 88/01058 | 2/1988 |
| WO | 98/01157 | 2/1989 |
| WO | 90/15070 | 9/1992 |

OTHER PUBLICATIONS

Sehon, In: Methods in Immunology and Immunochemistry. Ed. Williams and Chase.—NY: Academic Press, (1971). Chapter 15, p. 375–383.

Solsky and Rechnitz, Science, (1979) vol. 204, p. 1308–1309.

Nakamura and Tucker, In: Serum Protein Abnormalities, Ed. Ritzmann and Daniels, Little, Brown, & Co., Boston, (1975). Chapter 17, p. 314–330.

Casali et al., Journal of Immunology, (1989) vol. 143, p. 3476–3483.

Suenaga et al., Lupus, (1992) vol. 1, p. 363–368.

Conway de Macario et al., Journal of Immunol. Methods, (1983), vol. 59, p. 39–47.

Dissanayake et al., Immunology, (1977), vol. 32, p. 309–318.

Vonderviszt et al., Biochem. J., (1987) vol. 243, p. 449–455.

Litman et al., Clin. Chem., (1983) vol. 29, p. 1598–1603.

Ekins et al., In: Alternative Immunoassays, Ed. by. W.P. Collins, NY: Wiley (1985)., Chapter 13, p. 219–237.

Ekins et al., J. Endocrinology, 85(2):29P–30P (1980).

Giaver, Ivar: Journal of Immunology, (1976) vol. 116, No. 3, pp. 766–771.

Fodor et al., Science (1991) vol. 251, p. 767–773.

Pugia et al., J. Clin. Lab. Anal., (1999), vol. 13, p. 180–187.

D'Auria, Biomedical and Biophysical Research Communications (1999), vol. 263, p. 550–553.

William J. Dreyer, "What's New on the Horizton", pp. 1–5, New York conference on Apr. 26–27, 1982.

Declaration of Dr. Edwin F. Ullman from Nullity actions filed Oct. 15, 2003 against the German part of European Patents Nos. 0134215 and 0304202.

* cited by examiner

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–13 is confirmed.

Claims 14–15 are determined to be patentable as amended.

Claim 16, dependent on an amended claim, is determined to be patentable.

14. A binding assay process for [detecting the presence] *determining the concentration* of one or more target nucleic acid sequences in a liquid sample
using one or more capture binding agents comprising an oligonucleotide sequence capable of hybridizing to a given target nucleic acid sequence and a developing binding material comprising an oligonucleotide sequence capable of hybridizing to the bound target nucleic acid sequence,
the capture binding agent for a given target nucleic acid sequence being immobilized at high density in the form of one or more microspots each having an area less than 1 $mm^2$, and wherein
labelled microspheres having a diameter less than 5 μm are used in the assay in relation to the developing binding material, so that the signal from the label indicates the presence of the target nucleic acid sequence, thereby allowing the [presence] *concentration* of said one or more target nucleic acid sequences [detected] *determined*.

15. A kit for determining the concentration of one or more analytes in a liquid sample, the kit comprising:
one or more capture binding agents, each capture binding agent having binding sites specific for a given analyte expected to be present in the sample, wherein the capture binding agents are immobilized at high density on a support in the form of one or more microspots, each microspot having an area less than 1 $mm^2$; [and,]
one or more developing binding materials, each developing binding material being capable of binding to a given bound analyte, to binding sites of a given capture binding agent occupied by bound analyte or to binding sites of a given capture binding agent remaining unoccupied by the analyte; *and*
*one or more standard samples from which a dose-response curve is computed;*
wherein labelled microspheres having a diameter less than 5 μm are used in the assay in relation to the developing binding material, so that the strength of the signal from the label is representative of the fractional occupancy of the binding sites of a given capture binding agent, thereby allowing the concentration of the analyte to be determined *by comparison with a dose-response curve computed from said standard samples*.

* * * * *